United States Patent

Scheps

[11] Patent Number: 5,818,601
[45] Date of Patent: Oct. 6, 1998

[54] WAVELENGTH INDEPENDENT OPTICAL PROBE

[75] Inventor: Richard Scheps, Del Mar, Calif.

[73] Assignee: The United States of America as represented by the Secretary of the Navy, Washington, D.C.

[21] Appl. No.: 726,238

[22] Filed: Oct. 4, 1996

[51] Int. Cl.$^6$ ................................................. G01N 21/47
[52] U.S. Cl. ........................................................ 356/346
[58] Field of Search .................................. 356/445, 446; 385/11, 12; 372/98, 99, 101, 6, 22

[56] References Cited

U.S. PATENT DOCUMENTS

| | | |
|---|---|---|
| 3,740,155 | 6/1973 | Keller et al. ............................ 356/409 |
| 4,309,998 | 1/1982 | Aron nee Rosa et al. . |
| 4,397,310 | 8/1983 | Pomerantzeff . |
| 4,565,197 | 1/1986 | Daly . |
| 4,566,453 | 1/1986 | Kumano et al. . |
| 4,573,465 | 3/1986 | Sugiyama et al. . |
| 4,639,923 | 1/1987 | Tang et al. . |
| 4,862,888 | 9/1989 | Yessik . |
| 5,005,180 | 4/1991 | Edelman et al. . |
| 5,025,446 | 6/1991 | Kuizenga . |
| 5,125,924 | 6/1992 | Rudko . |
| 5,130,997 | 7/1992 | Ortiz et al. . |
| 5,134,622 | 7/1992 | Deacon . |
| 5,144,630 | 9/1992 | Lin . |
| 5,151,909 | 9/1992 | Davenport et al. . |
| 5,173,799 | 12/1992 | Tanuma . |
| 5,180,378 | 1/1993 | Kung et al. . |
| 5,181,214 | 1/1993 | Berger et al. ............................ 372/22 |
| 5,243,615 | 9/1993 | Ortiz et al. . |
| 5,247,389 | 9/1993 | Beausoleil . |
| 5,251,229 | 10/1993 | Bennett, Jr. et al. . |
| 5,257,274 | 10/1993 | Barrett et al. . |
| 5,260,953 | 11/1993 | Rowe . |
| 5,321,718 | 6/1994 | Waarts et al. . |
| 5,349,440 | 9/1994 | DeGroot ................................. 356/357 |
| 5,363,390 | 11/1994 | Yang et al. . |
| 5,390,204 | 2/1995 | Yessik et al. . |
| 5,390,210 | 2/1995 | Fouquet et al. . |
| 5,403,306 | 4/1995 | Edwards et al. . |
| 5,413,555 | 5/1995 | McMahan . |

FOREIGN PATENT DOCUMENTS

| | | | |
|---|---|---|---|
| 57-61935 | 4/1982 | Japan | ................................. 356/432 |
| 4-138326 | 5/1992 | Japan | ................................. 356/436 |

*Primary Examiner*—Frank G. Font
*Assistant Examiner*—Zandra V. Smith
*Attorney, Agent, or Firm*—Harvey Fendelman; Michael A. Kagan; Eric James Whitesell

[57] ABSTRACT

An optical probe for illuminating a location outside or inside a medical patient with a range of optical wavelengths appropriate to both diagnostic and surgical procedures comprises a polarization-preserving optical waveguide to conduct a polarized light beam to a polarizing beamsplitter, an optical detector to detect light deflected by the beamsplitter, a quarter-wave plate to couple the light between a non-refractive focusing element and a target, and a probe enclosure.

13 Claims, 1 Drawing Sheet

WAVELENGTH INDEPENDENT OPTICAL PROBE

BACKGROUND OF THE INVENTION

The present invention relates to optical probes such as those used in surgery. More specifically, but without limitation thereto, the present invention relates to an optical probe that may be used with optical sources spanning a wide range of optical wavelengths.

Laser-driven optical probes are currently used in various types of surgery, including eye surgery. An optical probe is a device for conducting light to a desired location outside or inside a medical patient for diagnostic and surgical purposes. Typical optical probes use a refractive lens to focus optical power into a small area. A disadvantage of these optical probes is that the refractive lenses used to focus the laser beam require refocusing for each wavelength of laser light used. For applications that may require a wide range of optical wavelengths, an optical probe that is substantially independent of the laser beam wavelength is needed.

SUMMARY OF THE INVENTION

The wavelength independent optical probe of the present invention is directed to overcoming the problems described above, and may provide further related advantages. No embodiment of the present invention described herein shall preclude other embodiments or advantages that may exist or become obvious to those skilled in the art.

The wavelength independent optical probe of the present invention comprises an optical waveguide, a polarizing beamsplitter, an optical detector, a quarter-wave plate, a focusing mirror, and a probe enclosure.

An advantage of the wavelength independent optical probe of the present invention is that a wide range of optical wavelengths may be accommodated by a single optical probe without requiring refocusing or realignment of the probe components.

Another advantage is that the same location may be illuminated by light having a number of different wavelengths without having to remove the probe for adjustment.

Yet another advantage is that the probe may be incorporated into an articulating arm for precision positioning control.

The features and advantages summarized above in addition to other aspects of the present invention will become more apparent from the description, presented in conjunction with the following drawings.

DESCRIPTION OF THE INVENTION

The following description is presented solely for the purpose of disclosing how the present invention may be made and used. The scope of the invention is defined by the claims.

Figure 1:
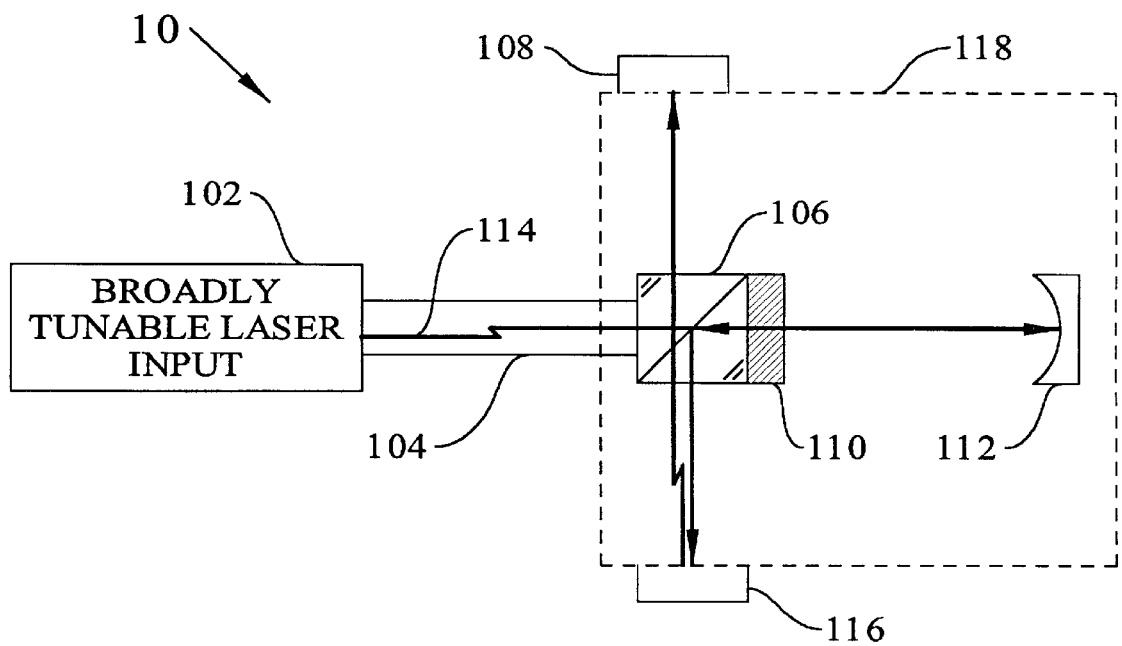
FIG. 1 is a side view of an optical probe of the present invention.

In FIG. 1 a wavelength independent optical probe assembly 10 comprises an optical waveguide 104, a polarizing beamsplitter 106, an optical detector 108, a quarter-wave plate 110, and a non-refractive focusing element 112. A probe enclosure 118 may be used to hold the components of the optical probe in alignment and to insert the probe assembly into a medical patient to reach a target 116. Probe enclosure 118 may be made to be replaceable by an additional disposable shell or other well known means. Optical waveguide 104 may be, for example, a polarization-preserving fiberoptic cable. Preserving polarization through optical waveguide 104 eliminates the need for a polarizer in optical probe assembly 10, thus avoiding a decrease in the available light power. Beamsplitter 106 is preferably a broadband polarizing beamsplitter such as a GLAN-Thompson prism, for example. Quarter-wave plate 110 may be made according to well known techniques and composed of a material such as mica or quartz crystal. Non-refractive focusing element 112 may be, for example, a broadband reflective concave mirror such as a front surface metallic mirror. In operation, an optical source 102 generates a polarized light beam 114 into optical waveguide 104. Optical source 102 may be, for example, an optical parametric oscillator such as a β-barium borate (BBO) crystal pumped by the third harmonic (355 nm) of a Nd:YAG laser or the tunable solid-state laser described in U.S. Pat. No. 5,260,953 issued on Nov. 9, 1993 to Rowe included herein by reference thereto. Optical waveguide 104 directs beam 114 into polarizing beamsplitter 106. Beamsplitter 106 is oriented to transmit beam 114 through quarter-wave plate 110 to focusing element 112. Beam 114 is reflected by focusing element 112 back through quarter-wave plate 110 and reflected by polarizing beamsplitter 106 to target 116. Target 116 scatters beam 114 to cause a portion of beam 114 to be transmitted through polarizing beamsplitter 106 to reach optical detector 108. Optical detector 108 may be, for example, a camera, a video camera, or a human eye.

Alternatively, quarter-wave plate 110 may be omitted to allow a portion of light beam 114 exiting from optical waveguide 104 along with the scattered portion of beam 114 to be transmitted to optical detector 108. In this arrangement, optical detector 108 may be positioned to receive only the scattered light to protect optical detector 108 from receiving excessive light power. Also, a the surface of beamsplitter 106 facing optical detector 108 may be masked to block the direct light from light beam 114.

Figure 2:
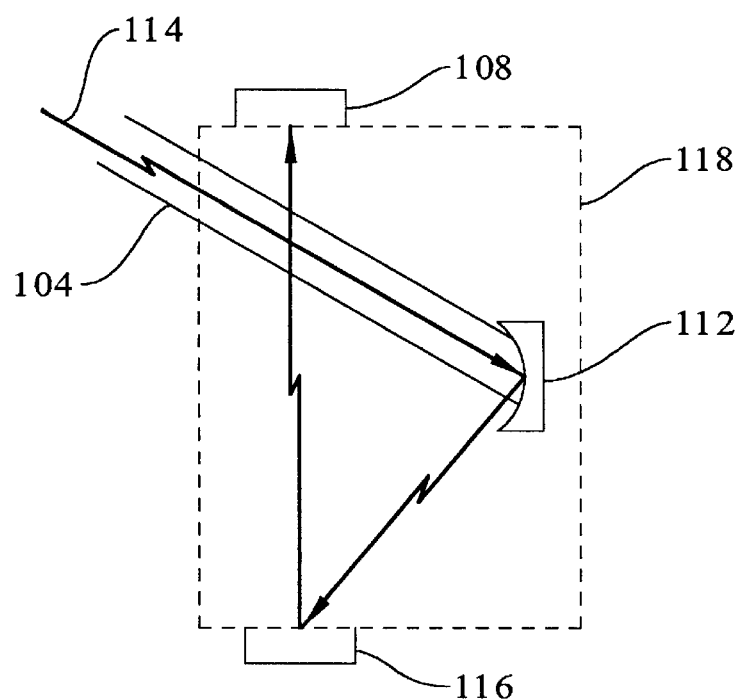
FIG. 2 is a side view of an alternate configuration of the optical probe of FIG. 1.

FIG. 2 illustrates an alternative arrangement using only non-refractive focusing element 112 to focus light beam 114 onto target 116. A portion of beam 114 is scattered by target 116 and directed to optical detector 108.

Other modifications, variations, and applications of the present invention may be made in accordance with the above teachings other than as specifically described to practice the invention within the scope of the following claims.

I claim:

1. An optical probe comprising:
   an optical waveguide;
   a polarizing beamsplitter coupled to said optical waveguide;
   a quarter-wave plate coupled to said polarizing beamsplitter; and
   a non-refractive focusing element coupled to said quarter-wave plate.

2. The optical probe of claim 1 further comprising an optical detector coupled to said polarizing beamsplitter.

3. The optical probe of claim 1 further comprising a probe enclosure coupled to said optical waveguide.

4. The optical probe of claim 3 wherein said probe enclosure is replaceable.

5. The optical probe of claim 4 wherein said optical source is a laser.

6. The optical probe of claim 4 wherein said optical source is an optical parametric oscillator.

7. The optical probe of claim 6 wherein said optical parametric oscillator is pumped by a laser.

8. The optical probe of claim 7 wherein said laser is a tunable laser.

9. The optical probe of claim 1 further comprising an optical source coupled to said optical waveguide.

10. The optical probe of claim 9 wherein said laser is a tunable laser.

11. The optical probe of claim 1 wherein said non-refractive focusing element is a broadband reflective concave mirror.

12. The optical probe of claim 1 wherein said optical waveguide is a fiberoptic cable.

13. The optical probe of claim 12 wherein said fiberoptic cable is polarization-preserving.

* * * * *